(12) United States Patent
Weber (10) Patent No.: US 7,810,045 B2
(45) Date of Patent: Oct. 5, 2010

(54) CONFIGURABLE USER INTERFACE SYSTEM FOR PROCESSING PATIENT MEDICAL DATA

(75) Inventor: Ellen Elizabeth Weber, Salt Lake City, UT (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 669 days.

(21) Appl. No.: 11/850,054

(22) Filed: Sep. 5, 2007

(65) Prior Publication Data

US 2008/0065422 A1     Mar. 13, 2008

Related U.S. Application Data

(60) Provisional application No. 60/824,813, filed on Sep. 7, 2006.

(51) Int. Cl.
G06F 3/048     (2006.01)
(52) U.S. Cl. .................. 715/792; 705/2; 705/3
(58) Field of Classification Search ................. 715/792; 705/2, 3
See application file for complete search history.

(56) References Cited

U.S. PATENT DOCUMENTS

| | | | |
|---|---|---|---|
| 5,447,164 A * | 9/1995 | Shaya et al. ................ | 600/523 |
| 6,405,195 B1 | 6/2002 | Ahlberg | |
| 6,542,910 B2 | 4/2003 | Cork et al. | |
| 2002/0065686 A1 * | 5/2002 | Monteleone et al. ........... | 705/3 |
| 2002/0082870 A1 * | 6/2002 | Penny et al. ................... | 705/3 |
| 2002/0116226 A1 * | 8/2002 | Auer et al. ..................... | 705/3 |
| 2003/0050800 A1 | 3/2003 | Brandt et al. | |
| 2003/0060688 A1 * | 3/2003 | Ciarniello et al. ........... | 600/300 |
| 2003/0131026 A1 | 7/2003 | Cork et al. | |
| 2005/0015279 A1 * | 1/2005 | Rucker ......................... | 705/2 |
| 2005/0108050 A1 * | 5/2005 | Knapheide ..................... | 705/2 |
| 2006/0078867 A1 * | 4/2006 | Penny et al. ................ | 434/353 |
| 2006/0085223 A1 * | 4/2006 | Anderson et al. .............. | 705/2 |
| 2006/0106641 A1 | 5/2006 | Bartsch et al. | |
| 2006/0242143 A1 * | 10/2006 | Esham et al. .................. | 707/6 |
| 2008/0004818 A1 * | 1/2008 | Zaleski ....................... | 702/50 |

* cited by examiner

*Primary Examiner*—Weilun Lo
*Assistant Examiner*—Rashedul Hassan (57) ABSTRACT

A system provides an improved clinician workflow by providing a composite display image supporting documenting clinical actions, reviewing previous actions and other clinical information and automatically indicating impact of changed clinician data on worker task lists. A user interface system for processing and displaying patient medical information includes at least one repository of information including clinical observation data comprising clinical observations of a particular patient and healthcare worker task data indicating tasks for performance by a healthcare worker. A display generator generates data representing a single composite display image incorporating multiple different image window areas. The multiple different image window areas include a first window area for presenting the clinical observation data and a second window area for presenting the healthcare worker task data and the display image supports user entry of a clinical observation item to change the clinical observation data in the first window area. A data processor detects a clinical observation in the first window is changed and automatically initiates change of the healthcare worker task data in the second window area, in response to the detection.

13 Claims, 6 Drawing Sheets

CONFIGURABLE USER INTERFACE SYSTEM FOR PROCESSING PATIENT MEDICAL DATA

This is a non-provisional application of provisional application Ser. No. 60/824,813 filed Sep. 7, 2006, by E. E. Weber.

FIELD OF THE INVENTION

This invention concerns a user interface system for processing and displaying patient medical information using different image window areas presenting healthcare worker task data and clinical observation data and managing associated data interaction.

BACKGROUND OF THE INVENTION

Hospitals process patient clinical information and manage healthcare worker tasks in response to the clinical information. Known systems typically process patient healthcare data by separating the viewing of data from the functions supporting actions on the clinical information. The functions supporting action on the data are accessed through numerous clicks and displays of screens and do not provide a consolidated secure, user defined image display with associated clinical actions and tasks. The image displays typically show a subset of data selected by a user that is currently active.

Known systems require a burdensome number of displays and user navigational commands (e.g., mouse clicks) before a user is able to initiate an action involving processing the data. This results in impeding a hospital clinical administrative and treatment process. In order to assess an impact of an action, a user needs to select another view of a different subset of data or return to a display only view of the data, for example. A system according to invention principles addresses these deficiencies and related problems.

SUMMARY OF THE INVENTION

A system provides an improved clinician workflow by providing a single location (image display) to make changes, document clinical actions, review previous actions and other clinical information and allows a clinician to see the impact of clinician actions on the data and task lists displayed (and data interaction) within the same page that contains other subsets of medical information substantially immediately after having initiated an action. A user interface system for processing and displaying patient medical information includes at least one repository of information including clinical observation data comprising clinical observations of a particular patient and healthcare worker task data indicating tasks for performance by a healthcare worker. A display generator generates data representing a single composite display image incorporating multiple different image window areas. The multiple different image window areas include a first window area for presenting the clinical observation data and a second window area for presenting the healthcare worker task data and the display image supports user entry of a clinical observation item to change the clinical observation data in the first window area. A data processor detects a clinical observation in the first window is changed and automatically initiates change of the healthcare worker task data in the second window area, in response to the detection.

DETAILED DESCRIPTION OF THE INVENTION

A system allows a clinician to securely take action and record data indicating actions taken in processing a user defined subset of medical data of a patient by providing a composite display image presenting multiple subsets of a patient medical data within an optional, user defined timeframe. The inventors have advantageously recognized that it is desirable to provide a system that allows rapid access to view, modify, add or delete patient (e.g., clinical) data and see resulting impact on other relevant data with a user friendly consolidated image display view (i.e., requiring minimal key strokes or mouse clicks). The system ensures that worker and device workflow is optimized by minimizing the number of times that a UI context needs to be changed to complete clinician tasks. The system improves clinician workflow by use of the composite display image as a single location to make changes, document clinical actions, review previous actions and other clinical information. The composite display image automatically shows impact of a clinical action in the clinical data as well as on worker tasks and task lists displayed within the composite display comprising subsets of medical information. Such impact occurs substantially immediately after a clinical action is taken. The system provides rules to ensure that new clinical actions are performed in the right order, with the right authority, avoiding duplication and ensuring comprehensive clinical action data entry.

A processor, as used herein, operates under the control of an executable application to (a) receive information from an input information device, (b) process the information by manipulating, analyzing, modifying, converting and/or transmitting the information, and/or (c) route the information to an output information device. A processor may use, or comprise the capabilities of, a controller or microprocessor, for example. The processor may operate with a display processor or generator. A display processor or generator is a known element for generating signals representing display images or portions thereof. A processor and a display processor may comprise a combination of, hardware, firmware, and/or software.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A user interface (UI), as used herein, comprises one or more display images, generated by a display processor and enabling user interaction with a processor or other device and associated data acquisition and processing functions.

The UI also includes an executable procedure or executable application. The executable procedure or executable application conditions the display processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity. Workflow comprises a sequence of tasks performed by a device or worker or both. An object or data object comprises a grouping of data, executable instructions or a combination of both or an executable procedure.

A workflow processor, as used herein, processes data to determine tasks to add to a task list, remove from a task list or modifies tasks incorporated on, or for incorporation on, a task list. A task list is a list of tasks for performance by a worker or device or a combination of both. A workflow processor may or may not employ a workflow engine. A workflow engine, as used herein, is a processor executing in response to predetermined process definitions that implement processes responsive to events and event associated data. The workflow engine implements processes in sequence and/or concurrently, responsive to event associated data to determine tasks for performance by a device and or worker and for updating task lists of a device and a worker to include determined tasks. A process definition is definable by a user and comprises a sequence of process steps including one or more, of start, wait, decision and task allocation steps for performance by a device and or worker, for example. An event is an occurrence affecting operation of a process implemented using a process definition.

A Workflow Management System is a software system that manages processes. It includes a process definition function that allows users to define a process that is to be followed, an Event Monitor, which captures events from a Healthcare Information System and communicates the results to the Workflow Management System. A processor in the Management System tracks which processes are running, for which patients, and what step needs to be executed next, according to a process definition. The Management System includes a procedure for notifying clinicians of a task to be performed, through their worklists (task lists) and a procedure for allocating and assigning tasks to specific users or specific teams. A document or record comprises a compilation of data in electronic form and is the equivalent of a paper document and may comprise a single, self-contained unit of information.

Figure 1:
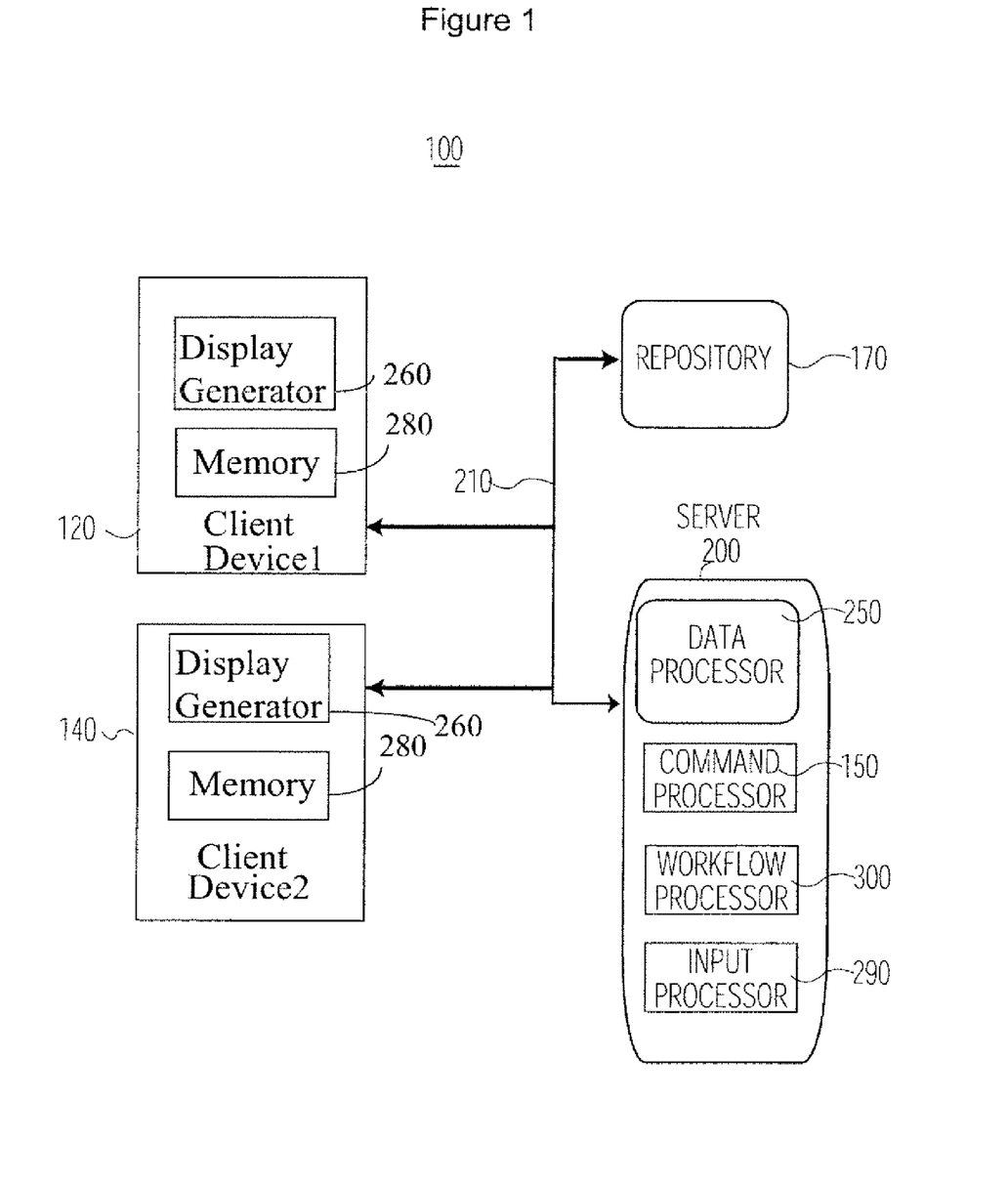
FIG. 1 shows a user interface system for processing and displaying patient medical information, according to invention principles.

FIG. 1 shows user interface system 100 for processing and displaying patient medical information. User interface system 100 includes client devices (workstations) 120 and 140, repository 170 and server 200 bidirectionally communicating via network 210. Information in repository 170 includes clinical observation data comprising clinical observations of a particular patient and healthcare worker task data indicating tasks for performance by a healthcare worker. Display generator 260 in client device 120 (or client device 140) comprising workstations, for example, generates data representing a single composite display image. The single composite display image incorporates multiple different image window areas including a first window area for presenting the clinical observation data and a second window area for presenting the healthcare worker task data and the single composite display image supports user entry of a clinical observation item to change the clinical observation data in the first window area. Data processor 250 detects a clinical observation in the first window is changed and automatically initiates change of the healthcare worker task data in the second window area, in response to detecting a clinical observation in the first window is changed. Workflow processor 300 in server 200 manages addition, deletion and modification of tasks to be performed by a worker or device as well as presentation of task lists in a window area in the composite display image.

Display generator 260 generates data representing a configuration display image enabling a user to configure the single composite display image incorporating a first plurality of different image window areas including medical information concerning a patient. The configuration display image includes a corresponding first plurality of image areas enabling a user to individually select data for display in each of the first plurality of different image window areas from multiple different types of dataset including at least two of (a) a vital signs dataset, (b) laboratory test results dataset, (c) a patient assessment information dataset, (d) fluid intake and output data dataset and (e) a healthcare worker task dataset. Command processor 150 initiates storage of configuration data representing a selected single composite display image configuration derived using the configuration display image.

System 100 provides a user with a secure user determined composite display image comprising a consolidated view of individual patient information and enables a user to initiate processing of a subset of patient medical data within an optional, user defined timeframe. The composite display image in various embodiments, enables a user to update patient demographic information, add a clinical observation and a collection of clinical observations in a user defined group, to displayed patient clinical data. The composite display image in one or more embodiments, enables a user to renew medicine orders for administration to a patient, place orders, revise orders, update orders, hold or cancel existing orders and acknowledge Physician placed orders. The composite display image also enables a user to update medication administration details, update plans of care (e.g., treatment plans) and customize a treatment protocol such as by adding goals, outcomes, and or interventions to a plan of care and update patient progress compared with a treatment protocol. The composite display image enables a user to request information from ancillary departments such as Pharmacy, Laboratory and Radiology departments, enter progress notes and document medication administration using an electronic signature, for example. Workflow processor 300 in server 200 manages addition, deletion and modification of tasks to be performed by a worker or device as well as presentation of task lists in a window area in the composite display image. Workflow processor 300 adds a task list representative item to a worker or device task list in a window area in the composite display image, moves an item to a task list of another clinician and marks items that are complete, held or deleted from a task list.

System 100 advantageously enables a clinician to concurrently view subsets of clinical data of a patient in different window areas of a composite display image and initiate processing data of one of the subsets of data displayed substantially immediately. The data processing includes automatically updating and refreshing a current data subset along with other subsets of data displayed, reflecting the impact of clinician initiated processing of data in a patient health record. System 100 addresses a problem that each clinical specialty (e.g., cardiology, radiology, oncology etc.) needs to review the subset of data that is appropriate to the specific clinical focus of the specialty. System 100 allows each user to define and view, review, modify, update, append or delete patient clinical data associated with the user while concurrently viewing a specialty clinical view.

Figure 2:
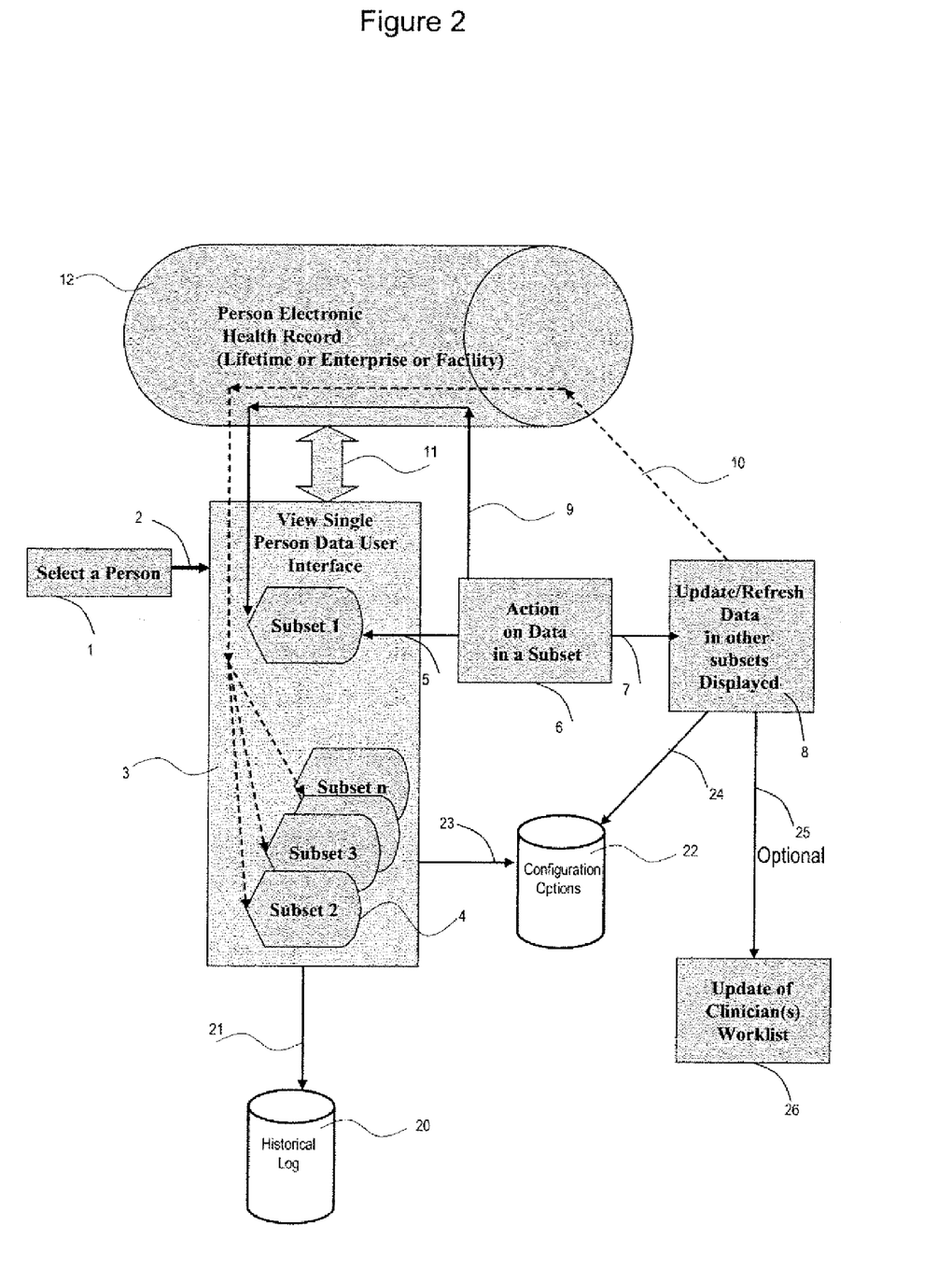
FIG. 2 shows operational data and command flow of a user interface system for processing and displaying patient medical information, according to invention principles.

FIG. 2 shows operational data and command flow of a user interface system for processing and displaying patient medical information. A user selects a patient (1) and requests presentation of a composite (Quick Overview) display image (a View of Single Patient Data User Interface image) (3) via link (2). The single composite (Quick Overview) display image (3) incorporates multiple different image window areas e.g., four in a quadrant. The different image window areas present different individual corresponding subsets of data derived from one or more data sources in response to stored configuration data. In one embodiment four quadrant window areas in single composite (Quick Overview) display image (3) present information acquired from Patient Electronic Health Record (12) using interface (11). The four quadrant window areas show corresponding subsets (4) of data identified in configuration data in configuration database (22) accessed through interface (23). The single composite (Quick Overview) display image (3) places each of the assigned quadrants subset of information (4) into a corresponding location in display image (3).

Figure 3:
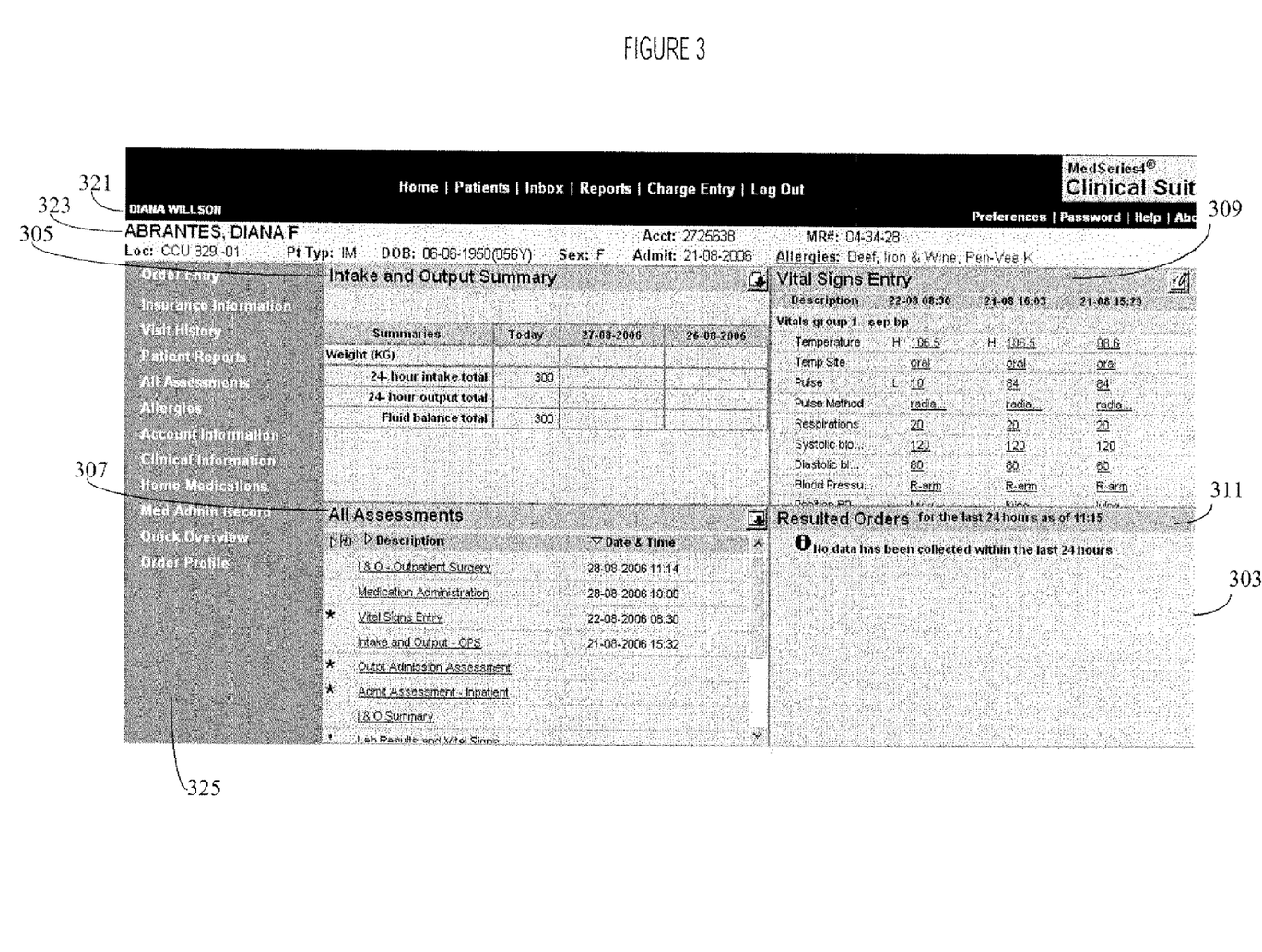
FIG. 3 shows a single composite (data overview) display image provided by the user interface system for processing and displaying patient medical information, according to invention principles.

FIG. 3 shows single composite (Quick Overview) display image 303 provided by user interface system 100 for processing and displaying patient medical information. In this embodiment, image 303 includes four window areas 305, 307, 309 and 311 presenting different individual corresponding subsets of data to an identified user 321 concerning an identified patient 323. The subsets of data comprise intake and output summary data, a patient assessment record list, vital signs (entered by a user) and resulting medication orders for administration to the patient, respectively, for example. The subsets of data are acquired by input processor 290 (FIG. 1) from one or more data sources in response to configuration data stored in repository 170. Column 325 (FIG. 3) lists links to other patient related data and function screens accessible by physician 321 including, an order entry screen, insurance information, visit history, patient reports, assessments, allergies, account information, clinical information, home medications, received medications and order profile in addition a link to the single composite (Quick Overview) display image 303.

Continuing with FIG. 2 operation, if a user initiates a processing action involving specific information in e.g., quadrant four window areas 305, 307, 309 and 311 (FIG. 3 and display image (3) of FIG. 2), the single composite (Quick Overview) display image (3) initiates processing by data processor 250 of a data Subset (6) via communication message (5). Data processor 250 processes a data Subset (6) using data acquired from Patient Electronic Health Record (12) via interface (9). In response to processing (add, modify, delete or update) of data subset records (6), data processor 250 executes to update and refresh (8) data in other displayed subsets via interface (7). Data processor 250 updates and refreshes (8) data in one or more particular data subsets in response to a user configuration or other command and thereby only updates specific quadrants or all quadrants, for example. The update configuration data is derived from configuration database (22) through interface (24). Also configuration options indicating configuration of subset data in display image (3) are stored in the configuration options database (22 or repository 170 of FIG. 1) and used through interface (23). These options may be set to optimize the visual performance or data processing performance of the system for a particular user. Data processor 250 in updating and refreshing (8) data subsets also updates a user task list (worklist) or adds or modifies other clinician tasks and task lists by initiating update process (26) through interface (25). The update of clinician task lists (26) adds, deletes, updates and modifies tasks and task lists upon execution of rules identifying tasks to be performed by device or worker in response to a specific clinical action. For example, if an update to a subset of data included change of a patient record to include an indicator indicating a patient needed isolation, an entry is placed by the system on task lists of other nurses assigned to care for the patient to inform the nurses of the isolation change for the patient.

The quadrant four window areas of single composite (Quick Overview) display image (3) are updated by acquisition of data via interface (10) from Patient Electronic Health Record (12) using interface (11) and newly updated content (4) is displayed in display image (3). Data indicating change and updates to the single composite (Quick Overview) display image (3) as well as data identifying source of the update data, a user and source computer address initiating the update, is recorded in historical log (20) through interface (21).

In the FIG. 2 system operation, a clinician selects a patient and system 100 (FIG. 1) displays a single composite (Quick Overview) display image containing one or more subsets of data retrieved from a patient electronic health record. The data subsets acquired from a patient electronic health record include vital signs, medication administration records, medication orders, progress notes, laboratory test results, nursing assessment findings, plan of care, clinical documentation, scheduled treatment procedures, scheduled medications to be administered, recorded fluid intake and output, diagnostic test results, orders for treatment to be administered to the patient, plans of care, treatment protocols and guidelines and task lists, for example. The clinician selects a subset of data to view and review and optionally updates and enters new clinical data. In response, relevant data in individual window areas of the single composite (Quick Overview) display image is refreshed to reflect current data content (including any modifications made).

Figure 4:
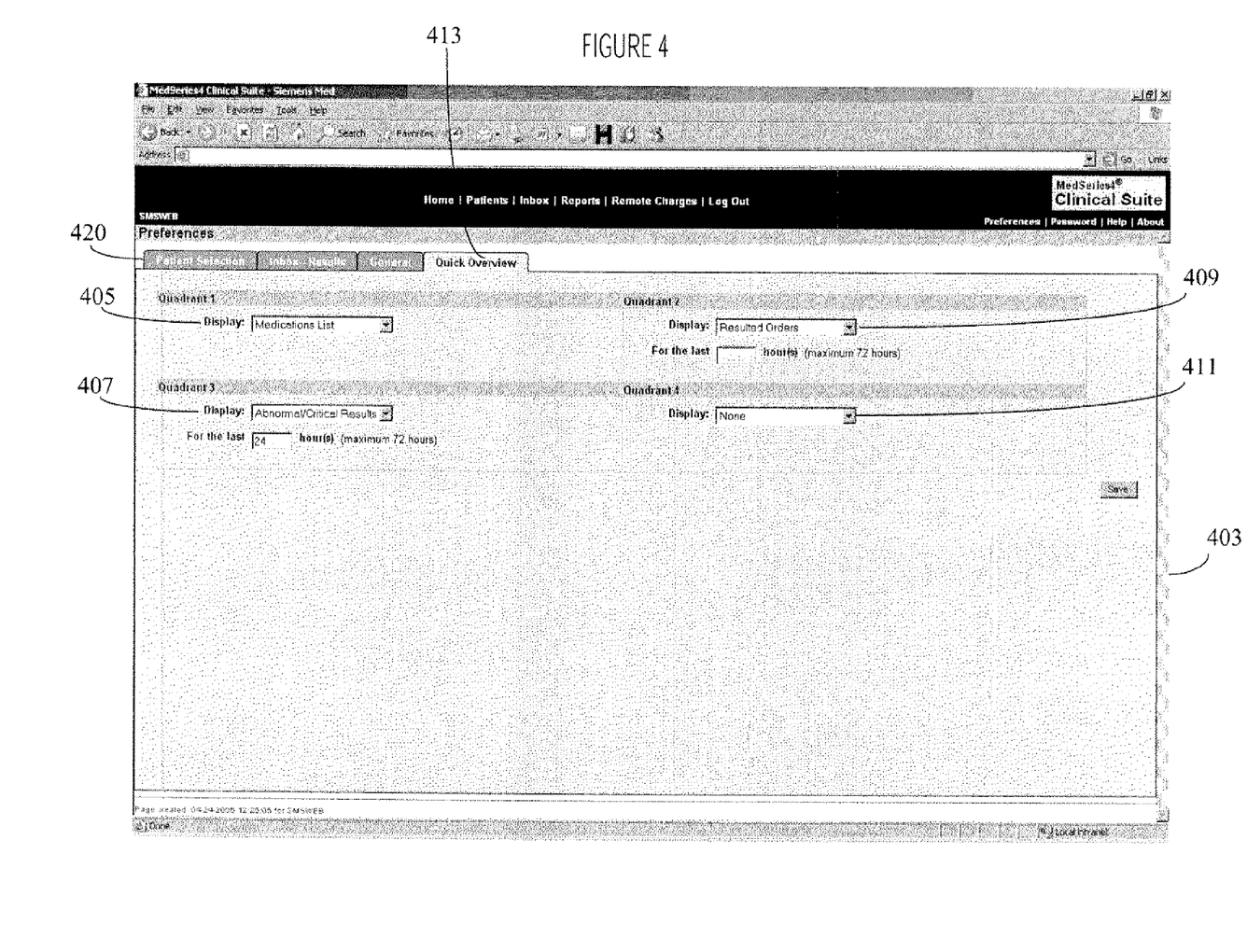
FIG. 4 shows a display image used for configuring a single composite (data overview) display image, according to invention principles.

FIG. 4 shows display image 403 used for configuring portions of a single composite (data overview) display image. Display image 403 is presented in response to user selection of Quick Overview tab 413 in tab row 420. Other tabs in row 420 enable a user to select images associated with functions including patient selection, inbox (e.g., of messages or tasks), patient results and general work related activities and data. In one embodiment mage 403 is used for configuring four quadrant window areas for displaying different patient related subsets of data in single composite (Quick Overview) display image (3 of FIG. 2). Specifically, a user selects a subset of data to be displayed in the four quadrant areas using elements 405, 407, 409 and 411. In another embodiment, display image (3) includes a different number of image window areas. Element 405 indicates a user has selected a medication list of a patient for display in a corresponding upper left quadrant of. Element 407 indicates a user has selected abnormal critical results of a patient occurring over the previous 24 hours for display in a corresponding lower left quadrant. Element 409 indicates a user has selected treatment orders for administration to a patient for display in a corresponding upper right quadrant. Element 411 indicates a user has not selected any subset of data for display in a corresponding lower right quadrant. Display image 403 enables an individual user to select a subset of patient data to be displayed in quadrants in single composite (Quick Overview) display image (3) for a particular patient. In another embodiment, display image 403 enables a user to configure display of subsets of data in the four quadrant window areas for up to four corresponding different patients. Elements 407 and 409 enable a user to select data acquired over a particular time period for display, such as a selected number of preceding hours. This time period selection reduces the amount of data to be reviewed by a clinician and is usable to emphasize the most recent patient information.

Figure 5:
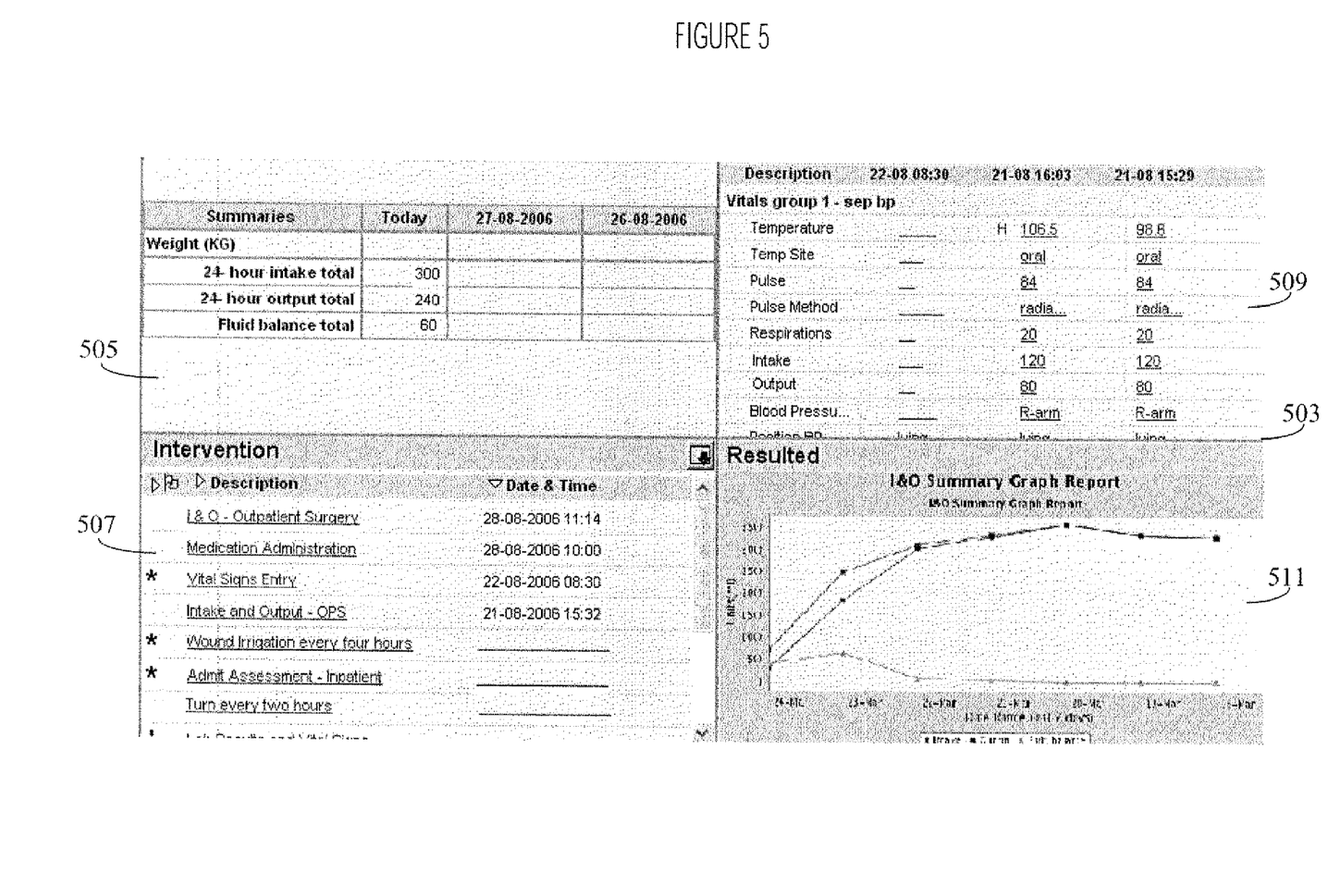
FIG. 5 shows a further single composite (data overview) display image provided by the user interface system, according to invention principles.

FIG. 5 shows single composite (data overview) display image 503 provided by User interface system 100 (FIG. 1). Image window areas 507 and 509 respectively and concurrently, enable user input of data and display task list data. Image window area 509 illustrates display and entry of patient observation data including for example, temperature, site of temperature measurement, pulse etc. Image window area 507 illustrates display and entry of the healthcare worker task list data and user entry of data indicating date and time of task completion. Data input via image window area 509 is advantageously automatically reflected both in the task list data presented in image window area 507 as well as in image window area 509. Data indicating tasks for performance (involving intervention) by a worker, are automatically added, deleted or modified in mage window area 507 in response to data entered via image window area 509 or data entered in image window area 507 itself. Image window areas 505, 507, 509 and 511 are individually configured by a healthcare worker to include data pertinent to a role that a healthcare worker is performing in caring for a patient.

Image window areas are configured to include either a combination of data entry fields and data display fields or just a single type of data, for example. A user is able to configure a single composite (Quick Overview) display image with image window areas including corresponding different combinations of patient data subsets to enable a healthcare worker to present data indicating a workflow to be used by the healthcare worker. Patient data subsets that may be incorporated in a window area include data indicating radiology results, medications administered, home medication regimes and patient allergies, for example. In addition, one or more window areas may indicate healthcare worker tasks that are advantageously dynamically updated as a result of data entered in other window areas of the single composite (Quick Overview) display image. Such other window areas may enable a user to review and sign medical data and associated forms or mark a healthcare worker task as being complete which may initiate the system to add a task to a healthcare worker or device task list.

Figure 6:
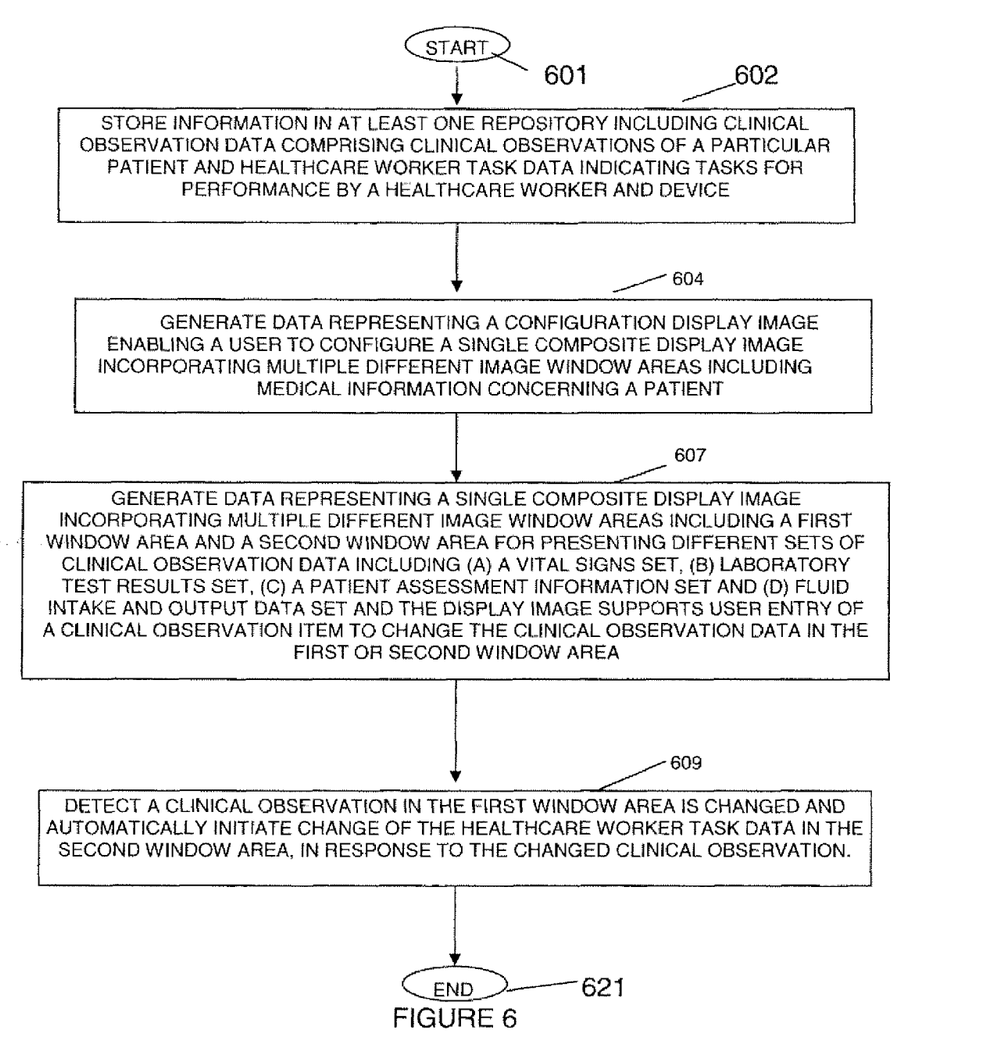
FIG. 6 shows a flowchart of a process performed by a user interface system for processing and displaying patient medical information, according to invention principles.

FIG. 6 shows a flowchart of a process performed by a user interface system 100 for processing and displaying patient medical information. The steps of FIG. 6 may be performed automatically. In step 602 following the start at step 601, data processor 250 (FIG. 1) stores information in at least one repository 170 including clinical observation data comprising clinical observations of a particular patient and healthcare worker and device task data indicating tasks for performance by a healthcare worker and device. In step 604, display generator 260 generates data representing a configuration display image enabling a user to configure a single composite display image incorporating a first plurality of different image window areas including medical information concerning a patient. The configuration display image includes a corresponding first plurality of configuration image areas enabling a user to individually select data for display in each of the first plurality of different image window areas from a plurality of different types of dataset including at least two of (a) a vital signs dataset, (b) laboratory test results dataset, (c) a patient assessment information dataset, (d) fluid intake and output data dataset and (e) a healthcare worker task dataset. In one embodiment, the different image window areas include a first window area for presenting clinical observation data and a second window area for presenting healthcare worker task data and the single composite display image supports user entry of a clinical observation item to change the clinical observation data in the first window area. Command processor 150 (FIG. 1) initiates storage of configuration data representing a selected single composite display image configuration derived using the configuration display image. The first plurality of configuration image areas has a sequence and approximate positional correspondence to the first plurality of different image window areas.

In step 607, display generator 260 generates data representing a single composite display image incorporating multiple different image window areas. The multiple different image window areas include a first window area and a second window area for presenting different sets of clinical observation data. The different sets include at least two of (a) a vital signs set, (b) laboratory test results set, (c) a patient assessment information set and (d) fluid intake and output data set. The display image supports user entry of a clinical observation item to change the clinical observation data in the first or second window area. In step 609 data processor 250 detects a clinical observation in the first window area is changed and automatically initiates change of healthcare worker task data in the second window area, in response to detecting a clinical observation in the first window is changed. Data processor initiates change of healthcare worker task data to include a task involving intervention by the healthcare worker in the care of a particular patient to address a condition associated with the change in the clinical observation data. The multiple different image window areas includes a third window area for presenting the healthcare worker task data and data processor 250 detects a clinical observation in the first window area is changed and automatically initiates change of the healthcare worker task data in the third window area, in response to a changed clinical observation. For this purpose data processor 250 uses repository 170 including mapping information mutually associating individual and combinations of, clinical observations with tasks, clinical actions, interventions and other data in other displayed image window areas within the single composite display image. Further, in one embodiment the plurality of different image window areas comprises at least four window areas.

In one embodiment, the different image window areas include a window area for presenting different sets of patient medical data, including, radiology results, medications administered, home medication regimes or patient allergies. Data processor 250 detects an item of a different set of patient medical data is changed and automatically initiates change of healthcare worker task data in the second window area, in response to detecting a changed item. The different image window areas also include a third window area for presenting orders for treatment to be administered to a patient and data processor 250 detects an item in the second or third window area is changed and automatically initiates change of data in any of the different image window areas, in response to detecting a changed item. The change in the item in the second or third window area comprises at least one of, (a) a change in orders and (b) indication a healthcare worker task is complete. A change in the item may also comprise a change in the second window area to indicate a healthcare worker task is complete and a resultant additional task is added. The process of FIG. 6 terminates at step 621.

The system and processes of FIGS. 1-6 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. System 100 improves the amount of related data concerning a single patient that is available to a clinician at one time and provides a clinician with substantially immediate feedback in response to processing patient clinical data. A single composite (Quick Overview) display image shows patient record subset data updates in context and related to other displayed data subsets. System 100 is usable by other systems which add, modify or view a subset of patient health data and is usable as an automated system for clinicians to add, modify or view a patient electronic health record. The processes and applications may in alternative embodiments, be located on one or more (e.g., distributed) processing devices accessing a network linking the elements of FIG. 1. Further, any of the functions and steps provided in FIGS. 1-6 may be implemented in hardware, software or a combination of both and may reside on one or more processing devices located at any location of a network linking the elements of FIG. 1 or another linked network including the Internet.

What is claimed is:

1. A user interface system for processing and displaying patient medical information, comprising:
   at least one repository of information including clinical observation data comprising clinical observations of a particular patient and healthcare worker task data indicating tasks for performance by a healthcare worker;
   a computer device comprising a memory and a display generator for generating data representing a single composite display image incorporating a plurality of different image window areas, said plurality of different image window areas including a first window area for presenting said clinical observation data and a second window area for presenting said healthcare worker task data and said single composite display image supports user entry of a clinical observation item to change said clinical observation data in said first window area; and
   a data processor for, detecting a clinical observation data in said first window area is changed and automatically initiating change of said healthcare worker task data in said second window area, in response to detecting said change of said clinical observation data;
   wherein said data processor initiates change of said healthcare worker task data to include a task involving intervention by said healthcare worker in the care of said particular patient to address a condition associated with said change of said clinical observation data.

2. A system according to claim 1, wherein
   said clinical observation data comprises at least one of, (a) vital signs, (b) laboratory test results, (c) patient assessment information and (d) fluid intake and output data.

3. A system according to claim 1, wherein
   said plurality of different image window areas includes said first window area and a third window area for presenting different sets of clinical observation data, said different sets including at least two of (a) a vital signs set, (b) laboratory test results set, (c) a patient assessment information set and (d) fluid intake and output data set and
   said data processor detects a clinical observation in one of said first or third window areas is changed and automatically initiates change of said healthcare worker task data in said second window area, in response to said changed clinical observation.

4. A system according to claim 1, wherein said plurality of different image window areas includes said first window area and a third window area for presenting different sets of clinical observation data, said different sets including at least two of (a) a vital signs set, (b) laboratory test results set, (c) a patient assessment information set and (d) fluid intake and output data set and said data processor detects a clinical observation in said first window area is changed and automatically initiates change of said healthcare worker task data in said second window area, in response to said changed clinical observation.

5. A system according to claim 1, wherein said different image window areas include a window area for presenting different sets of patient medical data, including at least one of (a) radiology results, (b) medications administered, (c) home medication regimes and (d) patient allergies and said data processor detects an item of a different set of patient medical data is changed and automatically initiates change of said healthcare worker task data in said second window area, in response to detecting a changed item.

6. A system according to claim 1, wherein
   said plurality of different image window areas include a third window area for presenting orders for treatment to be administered to a patient and
   said data processor detects an item in said second or third window area is changed and automatically initiates change of data in any of said plurality of different image window areas, in response to detecting a changed item.

7. A system according to claim 6, wherein
   said change in said item in said second or third window area comprises at least one of, (a) a change in orders and (b) indication a healthcare worker task is complete.

8. A system according to claim 6, wherein
   said change in said item comprises a change in said second window area to indicate a healthcare worker task is complete and a resultant additional task is added.

9. A user interface system for processing and displaying patient medical information, comprising:
   at least one repository of information including clinical observation data comprising clinical observations of a particular patient and healthcare worker task data indicating tasks for performance by a healthcare worker;
   a computer device comprising a memory and a display generator for generating data representing a single composite display image incorporating a plurality of different image window areas, said plurality of different image window areas including a first window area and a second window area for presenting different sets of clinical observation data, said different sets including at least two of (a) a vital signs set, (b) laboratory test results set, (c) a patient assessment information set and (d) fluid intake and output data set and said display image supports user entry of a clinical observation item to change said clinical observation data in said first or second window area; and a data processor for, detecting a clinical observation data in said first window area is changed and automatically initiating change of healthcare worker task data in said second window area, in response to detecting said change of said clinical observation data;

wherein said data processor initiates change of said healthcare worker task data to include a task involving intervention by said healthcare worker in the care of said particular patient to address a condition associated with said change of said clinical observation data.

10. A system according to claim 9, wherein said plurality of different image window areas includes a third window area for presenting said healthcare worker task data and said data processor detects a clinical observation in said first window area is changed and automatically initiates change of said healthcare worker task data in said third window area, in response to said changed clinical observation.

11. A system according to claim 9, wherein said plurality of different image window areas comprises at least four window areas.

12. A system for configuring a user interface for displaying patient medical information, comprising:

a computer device comprising a memory and a display generator for generating data representing a configuration display image enabling a user to configure a single composite display image incorporating a first plurality of different image window areas including medical information concerning a patient, said configuration display image including a corresponding first plurality of configuration image areas enabling a user to individually select data for display in each of said first plurality of different image window areas from a plurality of different types of dataset including at least two of (a) a vital signs dataset, (b) laboratory test results dataset, (c) a patient assessment information dataset, (d) fluid intake and output data dataset and (e) a healthcare worker task dataset;

a command processor for initiating storage of configuration data representing a selected single composite display image configuration derived using said configuration display image;

wherein said first plurality of configuration image areas has a sequence and approximate positional correspondence to said first plurality of different image window areas.

13. A system for configuring a user interface for displaying patient medical information, comprising:

a computer device comprising a memory and a display generator for generating data representing a configuration display image enabling a user to configure a single composite display image incorporating a plurality of different image window areas including a first window area for presenting clinical observation data and a second window area for presenting healthcare worker task data, said configuration display image including a corresponding plurality of configuration image areas enabling a user to individually select data for display in each of said plurality of different image window areas from a plurality of different types of dataset including healthcare worker task data and at least two of (a) a vital signs dataset, (b) laboratory test results dataset, (c) a patient assessment information dataset and (d) fluid intake and output data dataset;

a command processor for initiating storage of configuration data representing a selected single composite display image configuration derived using said configuration display image;

wherein said plurality of configuration image areas has a sequence and approximate positional correspondence to said plurality of different image window areas.

* * * * *